(12) United States Patent
O'Lenick, Jr.

(10) Patent No.: US 6,777,521 B1
(45) Date of Patent: Aug. 17, 2004

(54) SILICONE SULFATE POLYMERS

(75) Inventor: Anthony J. O'Lenick, Jr., Dacula, GA (US)

(73) Assignee: Siltech LLC, Dacula, GA (US)

( * ) Notice: Subject to any disclaimer, the term of this patent is extended or adjusted under 35 U.S.C. 154(b) by 0 days.

(21) Appl. No.: 10/395,605

(22) Filed: Mar. 25, 2003

(51) Int. Cl.$^7$ .............................................. C08G 77/28
(52) U.S. Cl. ......................... 528/30; 556/428; 528/29; 528/33; 528/40
(58) Field of Search ............................ 528/29, 30, 33, 528/40; 556/428

(56) References Cited

U.S. PATENT DOCUMENTS

| | | | | |
|---|---|---|---|---|
| 3,278,465 A | * | 10/1966 | Twitchett et al. | ........... 521/111 |
| 3,507,897 A | * | 4/1970 | Pike | ............................ 516/55 |
| 3,531,417 A | * | 9/1970 | Morehouse | .................. 516/55 |
| 3,707,492 A | * | 12/1972 | Morehouse | .................. 556/428 |
| 3,957,658 A | * | 5/1976 | Chiesa et al. | .................. 252/3 |
| 4,895,917 A | * | 1/1990 | Gruning | ...................... 528/10 |
| 4,960,845 A | | 10/1990 | O'Lencik | |
| 5,281,687 A | * | 1/1994 | Busch et al. | .................. 528/25 |

OTHER PUBLICATIONS

Zhou et al. "Cation transport polymer electrolytes. Siloxane comb polymers with pendant oligo–oxyethylene chains and sulphonate groups". Polymer Communications, 1989, vol. 30, pp. 52–55.*

* cited by examiner

*Primary Examiner*—Margaret G. Moore

(57) ABSTRACT

The present invention relates to a (a) novel silicone sulfate, (b) a method for preparation of said sulfate and (c) application of said sulfate in The compounds of the present invention are made by reacting certain epoxy containing silicone compounds and sodium sulfate under aqueous conditions. The resulting compound is quite stable and offers excellent foam in personal care applications.

16 Claims, No Drawings

SILICONE SULFATE POLYMERS

BACKGROUND OF THE INVENTION

Field of Invention

The present invention relates to a (a) novel silicone sulfate, (b) a method for preparation of said sulfate and (c) application of said sulfate in industrial and personal care applications.

The compounds of the present invention are made by reacting certain epoxy containing silicone compounds and a sodium sulfate under aqueous conditions. The resulting compound is quite stable and offers excellent foaming properties and is substantive to glass and porcelain. In addition, compounds of the present invention may also contain a pendant hydroxyl group, which alters the water solubility and emulsification properties of the compound. In a preferred embodiment the hydroxy containing group may also contain a polyoxyethylene group and a polyoxypropylene group. The ability to regulate the type of polyoxyalkylene group and amount present ill the silicone polymer results in a series of products ranging widely in water/oil solubility. The technology used to produce the compounds of the present invention is very flexible and allows us to prepare performance tailored molecules for specific applications.

Object of the Invention

It is the object of the present invention to sulfated silicone polymers that have low color, low odor, and produce high levels of copious foam in aqueous systems.

Description of the Arts and Practices

U.S. Pat. No. 4,960,845 October 1990, incorporated herein by reference, to O' Lenick, Jr. discloses the preparation dimethicone copolyol sulfates. The compounds of this technology are prepared by reacting a hydroxy containing silicone with a sulfating reagent, like sulfur trioxide. While the products are interesting there are several drawbacks. Firstly, the reaction with the aggressive sulfation reactant gives a product with dark color and mal odor. Secondly, we have discovered that there is functional improvement to be had by having a free hydroxyl group present in the molecule. This group improves wetting and solubilization.

The Invention

SUMMARY OF THE INVENTION

The compounds of the present invention are made by reacting certain epoxy containing silicone compounds and sodium sulfate under aqueous conditions. The resulting compound is quite stable and offers excellent foaming properties. In addition compounds of the present invention may also contain a pendant hydroxyl group, which alters the water solubility and emulsification properties of the compound. In a preffered embodiment the hydroxy containing group may also contain a polyoxyethylene group and a polyoxypropylene group. The ability to regulate the type of polyoxyalkylene group and amount present in the silicone polymer results in a series of products ranging widely in water/oil solubility. The technology used to produce the compounds of the present invention is very flexible and allows us to prepare performance tailored molecules for specific applications.

DETAILED DESCRIPTION OF THE INVENTION

The compounds of tile present invention have several key portions in the molecule. Those groups include (a) a sulfate group, (b) a hydroxy propyl linkage group to silicone polymer, and (c) a silicone polymer that contains water-soluble polyoxyalkylene groups. These groups and their positioning in the molecule result in unique properties for the molecule. These include emulsification properties, wetting properties, particularly for hydrophobic pigments, and a lubricious skin feel. This combination of properties has heretofore been unattainable in one molecule.

Compounds of the invention conform to the following structure:

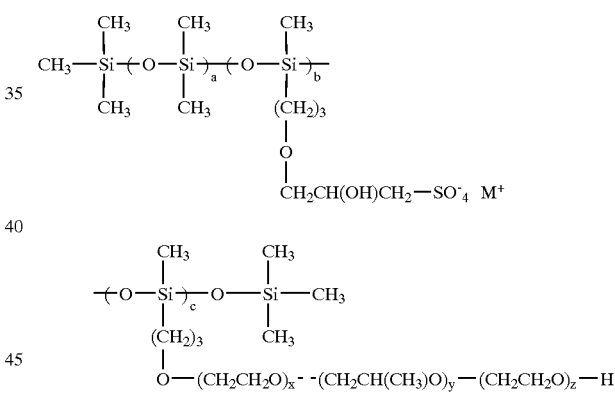

wherein;

a is an integer from 0 to 200;

b is an integer from 1 to 100;

c is an integer from 0 to 200;

x, y and z are integers and are independently ranging from 0 to 20;

M is selected from the group consisting of Na, K, and $NH_4$.

Illustrative of the sequence for the preparation of the compounds of the present is as follows;

In a 30% aqueous solution the disodium salt of a sulfate (pH 10.4) is reacted will an epoxy dimethicone copolyol to produce the sulfate of the present invention

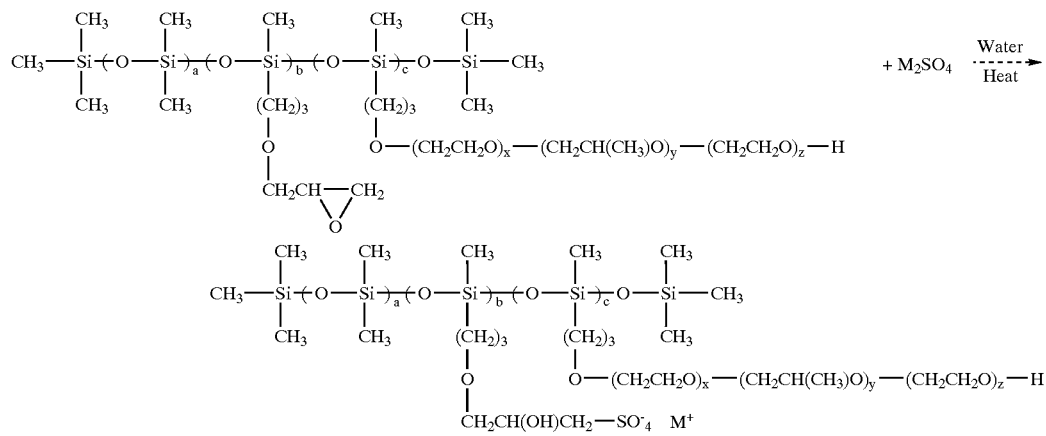

The compounds of the present invention are very good ingredients in a variety of applications that require the presence of both the sulfate and hydroxy group. These applications include personal care applications where the materials function as very mild detergents and foaming agents.

Preferred Embodiments

In a preferred embodiment x, y, and z are each zero.
In a preferred embodiment x ranges from 3 to 10.
In a preferred embodiment y ranges from 1 to 10.
In a preferred embodiment M is Na.
In a preferred embodiment M is K.
In a preferred embodiment M is $NH_4$.

EXAMPLES

Raw Materials

Epoxy Silicone Compounds

The silicone compounds useful as intermediates for the preparation of the compounds present invention are commercially available from Siltech LLC, Dacula Ga.

Inorganic Sulfates

Sulfate salts useful as intermediates for the preparation of the compounds present invention are commercially available from a variety of sources.

| Example | Compound |
|---------|----------|
| 8 | $Na_2SO_4$ |
| 9 | $K_2SO_4$ |
| 10 | $(NH_4)_2SO_4$ |

Preparation of the Products of the Present Invention

General Procedure

Into a suitable vessel equipped with thermometer, agitation and heating capabilities specified amount of water. Next the specified amount of sulfate is added under good agitation. The pH is adjusted to 10.3 with KOH if needed. The reaction mass is heated to 70–80° C. and epoxy silicone is added over I hour. The exotherm is watched so that the temperature does not exceed 95° C. If that temperature is reached, cooling is applied and the addition suspended.

| Example | a | b | c | x | y | z |
|---------|-----|-----|-----|----|----|----|
| 1 | 10 | 4 | 10 | 5 | 1 | 5 |
| 2 | 4 | 10 | 20 | 0 | 4 | 10 |
| 3 | 6 | 20 | 5 | 10 | 10 | 10 |
| 4 | 0 | 1 | 0 | 0 | 0 | 0 |
| 5 | 20 | 10 | 200 | 0 | 0 | 10 |
| 6 | 100 | 50 | 12 | 20 | 20 | 20 |
| 7 | 200 | 100 | 6 | 5 | 1 | 10 |

After the addition is complete the reaction mass is held at between 80–90° C. for four hours. During that time the % epoxide becomes vanishingly low.

Examples 11–24

Example 11

Into a suitable vessel equipped with thermometer, agitation and heating capabilities is added grams of water. Next add the specified number of grams of sulfate (Example 8) under good agitation. The pH is adjusted to 10.3 with the KOH. The reaction mass is heated to 70–80 degree. C. Next add grams of epoxy silicone (example 1). Addition is made over a 1 hour time period. The exotherm is watched so that the temperature does not exceed 95 degree. C.

After the addition is complete the reaction mass is held at between 80–90 degree. C. for four hours. During that time the % epoxide becomes vanishingly low.

Example 12–18

Example 11 is repeated, only this time the specified amount of water is added and the specified quantity and type of silicone epoxide and sulfate are added replacing the quantity and type in example 11.

|  | Epoxy Silicone |  | Sulfate |  | Water |
|---|---|---|---|---|---|
| Example | Example | Grams | Example | Grams | Grams |
| 12 | 1 | 1917 | 8 | 142 | 3089 |
| 13 | 2 | 1783 | 9 | 176 | 2939 |
| 14 | 3 | 578 | 10 | 132 | 1065 |
| 15 | 4 | 611 | 8 | 142 | 1129 |
| 16 | 5 | 11455 | 9 | 176 | 17450 |
| 17 | 6 | 1036 | 10 | 132 | 1755 |
| 18 | 7 | 3508 | 8 | 142 | 5475 |

The compounds of the present invention are in aqueous solution or emulsion and generally range from 20–60% solids. The preferred range is 30–40% solids. The products are used without purification. They are clear liquids having a light color.

APPLICATIONS

Urethane Foams as Modifiers of Bubble Structure

Traditional dimethicone copolyol compounds have been used in urethane foam. However, the ability to control the water-soluble groups and the hydroxyl containing groups independently from each other has been lacking. The compounds of the present invention have polyoxyalkylene groups present in two different and independent groups. This allows for the ability to tailor products that have the desired balance of polyoxyethylene groups, polyoxypropylene groups, hydroxyl groups and sulfate groups independently from each other. Sulfated surfactants are preferred in this application to phosphate groups due in part to the better foam stability.

Personal Care Applications for Mild Foam

The products of the present invention have copious foam and a very lubricious feel on the skin. They are high molecular weight, consequently do not penetrate the skin causing sting and irritation. Finally, the compounds have a sulfate group linked through a hydroxy linking group to a silicone.

What is claimed:

1. A silicone sulfate conforming to the following structure:

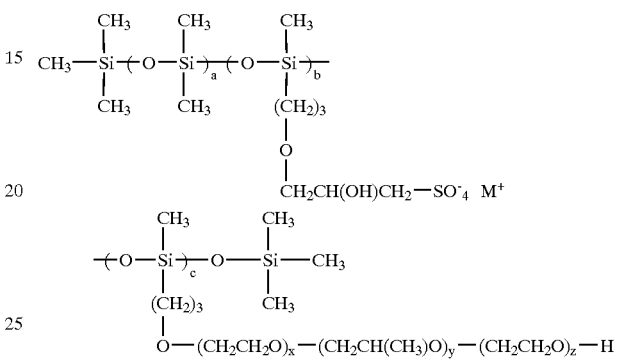

wherein:

a is an integer from 0 to 200;

b is an integer from 1 to 100;

c is an integer from 1 to 200;

x, y and z are integers and are independently ranging from 0 to 20;

M is selected from the group consisting of Na, K and $NH_4$.

2. A silicone sulfate of claim 1 wherein x, y, and z are each zero.

3. A silicone sulfate of claim 1 wherein x ranges from 3 to 10.

4. A silicone sulfate of clam 1 wherein y ranges from 1 to 10.

5. A silicone sulfate of claim 1 wherein M is Na.

6. A silicone sulfate of claim 1 wherein M is K.

7. A silicone sulfate of claim 1 wherein M is $NH_4$.

8. A silicone sulfate of claim 2 wherein M is Na.

9. A silicone sulfate of claim 2 wherein M is K.

10. A silicone sulfate of claim 2 wherein M is $NH_4$.

11. A silicone sulfate of claim 3 wherein M is Na.

12. A silicone sulfate of claim 3 wherein M is K.

13. A silicone sulfate of claim 3 wherein M is $NK_4$.

14. A silicone sulfate of claim 4 wherein M is Na.

15. A silicone sulfate of claim 4 wherein M is K.

16. A silicone sulfate of claim 4 wherein M is $NH_4$.

* * * * *